United States Patent
Richter et al.

[11] 3,940,259
[45] Feb. 24, 1976

[54] DIOXANE SUBSTITUTED-α-HALOANILIDES AS HERBICIDES

[75] Inventors: Sidney B. Richter, Chicago; John Krenzer, Oak Park, both of Ill.

[73] Assignee: Velsicol Chemical Corporation, Chicago, Ill.

[22] Filed: June 3, 1974

[21] Appl. No.: 475,461

Related U.S. Application Data

[62] Division of Ser. No. 357,746, May 7, 1973, Pat. No. 3,859,308.

[52] U.S. Cl.......................................... 71/88; 71/90
[51] Int. Cl.².................................... A01N 9/00
[58] Field of Search............................ 71/88

[56] References Cited
UNITED STATES PATENTS

| | | | |
|---|---|---|---|
| 3,344,148 | 9/1967 | Dietrich et al. | 71/88 |
| 3,547,620 | 12/1970 | Olin | 71/88 |
| 3,555,045 | 1/1971 | Griffith et al. | 71/88 |
| 3,644,422 | 2/1972 | Mine et al. | 71/88 |
| 3,663,200 | 5/1972 | Olin | 71/118 |
| 3,829,437 | 8/1974 | Zumach et al. | 71/88 |

FOREIGN PATENTS OR APPLICATIONS

| | | | |
|---|---|---|---|
| 492,682 | 8/1970 | Sweden | 71/88 |

*Primary Examiner*—Glennon H. Hollrah
*Attorney, Agent, or Firm*—Robert J. Schwarz; Dietmar H. Olesch

[57] ABSTRACT

This invention discloses new compounds of the formula

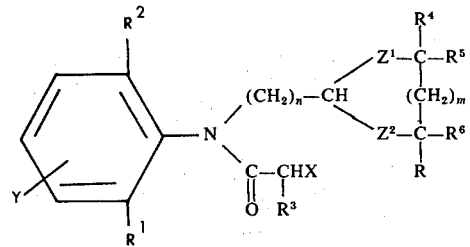

wherein Y is selected from the group consisting of hydrogen, lower alkyl and halogen; $R^1$ is selected from the group consisting of hydrogen, lower alkyl and lower alkoxy; $R^2$ is lower alkyl; $R^3$, $R^4$, $R^5$, $R^6$ and $R^7$ are independently selected from the group consisting of hydrogen and lower alkyl; X is halogen; $m$ is an integer from 0 to 2; $Z^1$ and $Z^2$ are independently selected from the group consisting of oxygen and sulfur; and n is an integer from 1 to 2. The compounds of the above description are useful as herbicides.

8 Claims, No Drawings

DIOXANE SUBSTITUTED-α-HALOANILIDES AS HERBICIDES

"This application is a division of copending application Ser. No. 357,746, filed May 7, 1973, now issued into U.S. Pat. No. 3,859,308."

This invention relates to new compositions of matter and more specifically relates to new compounds of the formula

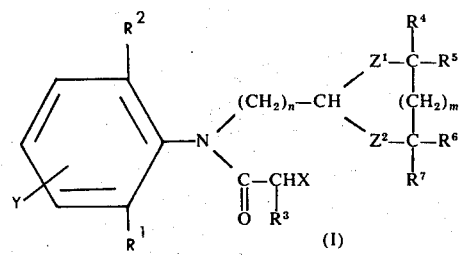

wherein Y is selected from the group consisting of hydrogen, lower alkyl and halogen; $R^1$ is selected from the group consisting of hydrogen, lower alkyl and lower alkoxy; $R^2$ is lower alkyl; $R^3$, $R^4$, $R^5$, $R^6$ and $R^7$ are independently selected from the group consisting of hydrogen and lower alkyl; X is halogen, m is an integer from 0 to 2; $Z^1$ and $Z^2$ are independently selected from the group consisting of oxygen and sulfur; and n is an integer from 1 to 2.

The term lower as used herein designates a straight or branched carbon chain of up of 4 carbon atoms.

The compounds of the present invention are unexpectedly useful as herbicides and are particularly useful in controlling grassy weeds.

In a preferred embodiment of the present invention Y is hydrogen, X is chlorine or bromine, and at least two of $R^4$, $R^5$, $R^6$ and $R^7$ are hydrogen.

The compounds of the present invention can be prepared by reacting a compound of the formula

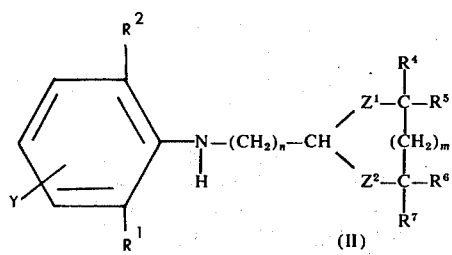

wherein Y, $R^1$, $R^2$, $R^4$, $R^5$, $R^6$, $R^7$, $Z^1$, $Z^2$, n and m are as heretofore described, with an α-haloalkanoyl chloride of the formula

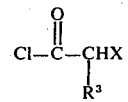

wherein X and $R^3$ are as heretofore described. This reaction can be effected by combining a compound of formula II with a compound of formula III in an inert organic reaction medium, such as dioxane, in the presence of an acid acceptor, such as an alkali metal carbonate or bicarbonate at a temperature of from about −10°C to about 25°C and stirring the resulting mixture for a period of about 15 to about 120 minutes. After this time the reaction mixture can be washed with water to remove inorganic salts and stripped of solvent to yield the desired product. This product can be used as such or can be further purified by recrystallization or other conventional means.

The compounds of formula II can be prepared by reacting a substituted aniline of the formula

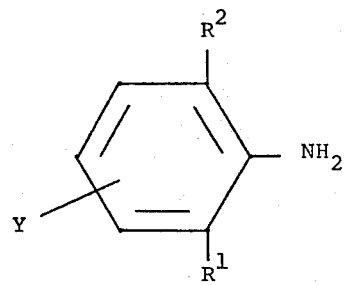

wherein Y, $R^1$ and $R^2$ are as heretofore described, with a compound of the formula

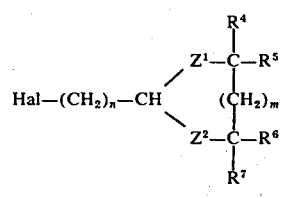

wherein Hal designates halogen such as chlorine or bromine and wherein $Z^1$, $Z^2$, $R^4$, $R^5$, $R^6$, $R^7$, n and m are as heretofore described. This reaction can be effected by combining a compound of formula IV with a compound of formula V in an inert organic reaction mixture such as dimethylformamide in the presence of an acid acceptor such as an alkali metal carbonate or bicarbonate and heating the resulting mixture at reflux for a period of from about 4 to about 48 hours. After this time the reaction mixture can be filtered and distilled to yield the desired product.

The compounds of formula V can be prepared by reacting an acetal of the formula

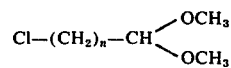

wherein n is as heretofore described, with a diol or dithiol of the formula

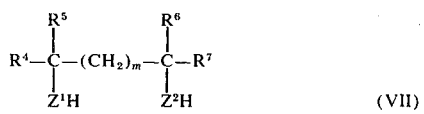

wherein $R^4$, $R^5$, $R^6$, $R^7$, $Z^1$, $Z^2$ and $m$ are as heretofore described. This reaction can be effected by combining the compound of formula VI with the compound of formula VII in about equimolar amounts and in the presence of an acid catalyst, such as sulfuric acid or toluene sulfonic acid, under anhydrous conditions. The mixture can be heated at reflux for a period of from about 1 to about 4 hours. After this time the reaction mixture can be distilled under reduced pressure to yield the desired product.

Exemplary diols and dithiols of formula VII useful for preparing the compounds of formula V are ethandiol-1,2, propandiol-1,2, propandiol-1,3, butandiol-1,2, butandiol-1,3, butandiol-1,4, butandiol-2,3, pentandiol-1,2, pentandiol-1,3, pentandiol-1,4, pentandiol-2,3, pentandiol-2,4, 2-methylpentandiol-2,4, 2-methylpropandiol-1,2, 2-methylbutandiol2,3, 3-methylbutandiol-1,3, hexandiol-1,2, hexandiol-1,3, hexandiol-1,4, hexandiol-2,3, hexandiol-2,4, hexandiol-2,5, hexandiol-3,4, 3-methylhexandiol-3,4, 3-ethylhexandiol-3,4, ethandithiol-1,2, propandithiol-1,2, propandithiol-1,3, butandithiol-1,2, butandithiol-1,3, butandithiol-1,4, butandithiol-2,3, pentandithiol-1,2 and the like.

Exemplary substituted anilines of formula IV useful for preparing the compounds of formula II are 2-methylaniline, 2-ethylaniline, 2-propylaniline, 2-isopropylaniline, 2-butylaniline, 2,6-dimethylaniline, 2,6-diethylaniline, 2,6-dipropylaniline, 2,6-dibutylaniline, 2-methoxy-6-methylaniline, 2-methoxy-6-ethylaniline, 2-ethoxy-6-methylaniline, 2-ethoxy-6-ethylaniline, 2-propoxy-6-methylaniline, 2-butoxy-6-ethylaniline, 2,4,6-trimethylaniline, 2,4,5-triethylaniline, 2,4,6-tripropylaniline, 2,6-dimethyl-4-butylaniline, 2,4-dimethylaniline, 2,4-diethylaniline, 2-methyl-4-chloroaniline, 2-ethyl-3-bromoaniline, 2,6-dimethyl-4-iodoaniline, 2,6-diethyl-4-chloroaniline and the like.

Exemplary α-haloalkanoyl chlorides of formula III are chloroacetyl chloride, bromoacetyl chloride, iodoacetyl chloride, α-chloropropanoyl chloride, α-bromopropanoyl chloride, α-chlorobutanoyl chloride, α-chloropentanoyl chloride, α-chlorohexanoyl chloride and the like.

The preparation of the compounds of the present invention is more specifically illustrated in the following examples.

EXAMPLE 1

Preparation of 2-Chloromethyl-1,3-dioxolane

The dimethyl acetal of 2-chloroacetaldehyde (125 grams; 1.0 mole) and ethandiol-1,2 (62 grams; 1.0 mole) are charged into a glass reaction flask equipped with a mechanical stirrer, thermometer and reflux condenser. Toluene sulfonic acid (0.3 grams) is added to the flask and the reaction mixture is refluxed for a period of about 2 hours. After this time the reaction mixture is distilled under aspirator partial pressure to remove methanol yielding the desired product 2-chloromethyl-1,3-dioxolane.

EXAMPLE 2

Preparation of N-(1,3-Dioxolan-2-ylmethyl)-2,6-dimethylaniline 2,6-Dimethylaniline (75 grams), 2-chloromethyl-1,3-dioxolane (25 grams), potassium carbonate (34 grams) and dimethylformamide (50 ml) were charged into a glass reaction vessel equipped with a mechanical stirrer, thermometer and reflux condenser. The reaction mixture was heated at reflux for a period of about 18 hours. After this time the mixture was filtered and distilled to yield the desired product N-(1,3-dioxolan-2-ylmethyl)-2,6-dimethylaniline.

EXAMPLE 3

Preparation of N-α-Chloroacetyl-N-(1,3-dioxolan-2-ylmethyl)2,6-dimethylaniline

N-(1,3-Dioxolan-2-ylmethyl)-2,6-dimethylaniline (7.8 grams), sodium bicarbonate (7.0 grams), dioxane (20 ml) and water (4 ml) were charged into a glass reaction vessel equipped with a mechanical stirrer and thermometer. The mixture was cooled to a temperature of about 0°C and chloroacetyl chloride (5.0 grams) was added, with stirring, over a period of about 15 minutes. After the addition was completed stirring was continued for a period of about 1 hour. After this time ether (100 ml) was added to the mixture and the resulting solution was washed with water. The washed solution was then dried over anhydrous magnesium sulfate and stripped of solvents leaving a solid residue. The residue was recrystallized from an ether-pentane mixture to yield the desired product N-α-chloroacetyl-N-(1,3-dioxolan-2-ylmethyl)-2,6-dimethylaniline having a melting point of 58° to 60°C.

EXAMPLE 4

Preparation of N-(1,3-Dioxolan-2-ylmethyl)-2,6-diethylaniline 2,6-Diethylaniline (75 grams; 0.5 mole), 2-chloromethyl-1,3-dioxolane (25 grams; 0.2 mole), potassium carbonate (22 grams; 0.2 mole) and dimethylformamide (50 ml) were charged into a glass reaction vessel equipped with a mechanical stirrer, thermometer and reflux condenser. The reaction mixture was heated, with stirring, for a period of about 18 hours. After this time the reaction mixture was filtered and then distilled to yield the desired product N-(1,3-dioxolan-2-ylmethyl)-2,6-diethylaniline.

EXAMPLE 5

Preparation of N-α-Chloroacetyl-N-(1,3-dioxolan-2-ylmethyl)-2,6-diethylaniline

N-(1,3-dioxolan-2-ylmethyl)-2,6-diethylaniline (7.7 grams), sodium bicarbonate (6.0 grams), dioxane (20 ml) and water (4 ml) were charged into a glass reaction vessel equipped with a mechanical stirrer and thermometer. This mixture was cooled to a temperature of about 0°C and chloroacetyl chloride (4.0 grams) was added, with stirring, over a period of about 15 minutes. After the addition was completed stirring was continued for a period of about 1 hour. After this time ether (100 ml) was added to the mixture and the resulting solution was washed with water. The washed solution was then dried over anhydrous magnesium sulfate and stripped of solvents leaving a solid residue. The residue was recrystallized from an ether-pentane mixture to yield the desired product N-α-chloroacetyl-N-(1,3-dioxolan-2-ylmethyl)-2,6-diethylaniline having a melting point of 86° to 87°C.

EXAMPLE 6

Preparation of
N-(1,3-Dioxolan-2-ylmethyl)2-methyl-5-chloroaniline

2-Methyl-5-chloroaniline (75 grams), 2-chloromethyl1,3-dioxolane (25 grams), potassium carbonate (22 grams) and dimethylformamide (50 ml) were charged into a glass reaction vessel equipped with a mechanical stirrer, thermometer, and reflux condenser. The reaction mixture was heated, with stirring, for a period of about 26 hours. After this time the reaction mixture was filtered and then distilled to yield the desired product N-(1,3-dioxolan-2-ylmethyl)-2-methyl-5chloroaniline having a boiling point of 116° to 118°C at 0.1 mm of Hg pressure.

EXAMPLE 7

Preparation of
N-α-Chloroacetyl-N-(1,3-dioxolan-2-ylmethyl)-2-methyl-5-chloroaniline N-(1,3-Dioxolan-2-ylmethyl)-2-methyl-5-chloroaniline (8 grams), sodium bicarbonate (7 grams), dioxane (50 ml) and water (4 ml) were charged into a glass reaction vessel equipped with a mechanical stirrer and thermometer. This mixture was cooled to a temperature of about 0°C and chloroacetyl chloride (4.3 grams) was added, with stirring, over a period of about 15 minutes. After the addition was completed stirring was continued for a period of about 1 hour. After this time ether (100 ml) was added to the mixture and the resulting solution was washed with water. The washed solution was then dried over anhydrous magnesium sulfate and stripped of solvents leaving a solid residue. The residue was recrystallized from hexane to yield the desired product N-α-chloroacetyl-N-(1,3-dioxolan-2-ylmethyl)-2methyl-5-chloroaniline having a melting point of 88° to 89°C.

EXAMPLE 8

Preparation of 2-Chloromethyl-1,3-dithiepane

The dimethyl acetal of 2-chloroacetaldehyde (125 grams; 1.0 mole) and butandithiol-1,4 (122 grams; 1.0 mole) are charged into a glass reaction vessel equipped with a mechanical stirrer, thermometer and reflux condenser. Toluene sulfonic acid (0.3 grams) is added to the reaction mixture and the mixture is refluxed for a period of about 2 hours. After this time the reaction mixture is distilled under aspirator pressure to yield the desired product 2-chloromethyl-1,3-dithiepane.

EXAMPLE 9

Preparation of
N-(1,3-Dithiepan-2-ylmethyl)2,6-diethylaniline 2,6-Diethylaniline (75 grams), 2-chloromethyl1,3-dithiepane (36.5 grams), potassium carbonate (34 grams) and dimethylformamide (75 ml) are charged into a glass reaction vessel equipped with a mechanical stirrer, thermometer and reflux condenser. The reaction mixture is heated at reflux for a period of about 18 hours. After this time the mixture is filtered and distilled to yield the desired product N-(1,3-dithiepan-2-ylmethyl)-2,6-diethylaniline.

EXAMPLE 10

Preparation of
N-α-Chloroacetyl-N-(1,3-dithiepan-2-ylmethyl)-2,6-diethylaniline

N-(1,3-Dithiepan-2-ylmethyl)-2,6-diethylaniline (15 grams), sodium bicarbonate (10 grams), dioxane (30 ml) and water (5 ml) are charged into a glass reaction vessel equipped with a mechanical stirrer and thermometer. The mixture is cooled to a temperature of about 0°C and chloroacetyl chloride (7 grams) is added, with stirring, over a period of about 15 minutes. After the addition is completed stirring is continued for a period of about 1 hour. After this time ether (100 ml) is added to the mixture and the resulting solution is washed with water. The washed solution is then dried over anhydrous magnesium sulfate and stripped of solvents leaving a solid residue. The residue is recrystallized to yield the desired product N-α-chloroacetyl-N-(1,3-dithiepan-2-ylmethyl)-2,6-diethylaniline.

EXAMPLE 11

Preparation of 2-Chloromethyl-1,3-dioxane

The dimethyl acetal of 2-chloroacetaldehyde (125 grams; 1.0 mole) and propandiol-1,3 (76 grams; 1.0 mole) are charged into a glass reaction vessel equipped with a mechanical stirrer, the thermometer and reflux condenser. Toluene sulfonic acid (0.3 grams) is added to the reaction mixture and the mixture is refluxed for a period of about 3 hours. After this time the reaction mixture is distilled under aspirator pressure to yield the desired product 2-chloromethyl-1,3-dioxane.

EXAMPLE 12

Preparation of
N-(1,3-dioxan-2-ylmethyl)-2,6-diethylaniline 2,6-Diethylaniline (75 grams), 2-chloromethyl-1,3-dioxane (14 grams), potassium carbonate (34 grams) and dimethylformamide (60 ml) are charged into a glass reaction vessel equipped with a mechanical stirrer, thermometer and reflux condenser. The reaction mixture is heated at reflux for a period of about 18 hours. After this time the mixture is filtered and distilled to yield the desired product N-(1,3-dioxan-2-ylmethyl)-2,6-diethylaniline.

EXAMPLE 13

Preparation of
N-α-Chloroacetyl-N-(1,3-dioxan-2-ylmethyl)-2,6-diethylaniline

N-(1,3-Dioxan-2-ylmethyl)-2,6-diethylaniline (25 grams), sodium bicarbonate (10 grams), dioxane (30 ml) and water (4 ml) are charged into a glass reaction vessel equipped with a mechanical stirrer and thermometer. The mixture is cooled to a temperature of about 0°C and chloroacetyl chloride (15 grams) is added, with stirring, over a period of about 15 minutes. After the addition is completed stirring is continued for a period of about 1 hour. After this time ether (100 ml) is added to the mixture and the resulting solution is washed with water. The washed solution is then dried over anhydrous magnesium sulfate and stripped of solvents leaving a solid residue. The residue is recrystallized to yield the desired product N-α-chloroacetyl-N-(1,3-dioxan2-ylmethyl)-2,6-diethylaniline.

EXAMPLE 14

Preparation of 2-Chloromethyl-1,3-dioxepane

The dimethyl acetal of 2-chloroacetaldehyde (125 grams; 1.0 mole) and butandiol-1,4 (90 grams; 1.0 mole) are charged into a glass reaction vessel equipped with a mechanical stirrer, thermometer and reflux condenser. Toluene sulfonic acid (0.3 grams) is added to the reaction mixture and the mixture is refluxed for a period of about 3 hours. After this time the reaction mixture is distilled under aspirator pressure to yield the desired product 2-chloro methyl-1,3-dioxepane.

EXAMPLE 15

Preparation of N-(1,3-Dioxepan-2-ylmethyl)-2,6-diethylaniline 2,6-Diethylaniline (75 grams), 2-chloromethyl1,3-dioxepane (15 grams), potassium carbonate (34 grams) and dimethylformamide (60 ml) are charged into a glass reaction vessel equipped with a mechanical stirrer, thermometer and reflux condenser. The reaction mixture is heated at reflux for a period of about 18 hours. After this time the mixture is filtered and distilled to yield the desired product N-(1,3-dioxepan-2-ylmethyl)-2,6-diethylaniline.

EXAMPLE 16

Preparation of N-α-Chloroacetyl-N-(1,3-dioxepan-2-ylmethyl)-2,6-diethylaniline

N-(1,3-dioxepan-2-ylmethyl)-2,6-diethylaniline (26.3 grams), sodium bicarbonate (15 grams), dioxane (30 ml) and water (4 ml) are charged into a glass reaction vessel equipped with a mechanical stirrer and thermometer. The mixture is cooled to a temperature of about 0°C and chloroacetyl chloride (15 grams) is added, with stirring, over a period of about 15 minutes. After the addition is completed stirring is continued for a period of about 1 hour. After this time ether (100 ml) is added to the mixture and the resulting solution is washed with water. The washed solution is then dried over anhydrous magnesium sulfate and stripped of solvents leaving a solid residue. The residue is recrystallized to yield the desired product N-α-chloroacetyl-N-(1,3-dioxepan-2-ylmethyl)-2,6-diethylaniline.

Additional compounds within the scope of the present invention can be prepared by the procedures detailed in the foregoing examples. In the following examples are given the essential starting materials required to prepare the indicated named compounds by the methods heretofore described.

EXAMPLE 17

The dimethyl acetal of 2-chloroacetaldehyde + ethandiol-1,2 + methylaniline + chloroacetyl chloride = N-α-chloroacetyl-N-(1,3-dioxolan-2-ylmethyl)-2-methylaniline.

EXAMPLE 18

The dimethyl acetal of 2-chloroacetaldehyde + ethandiol-1,2 + 2-ethylaniline + chloroacetyl chloride = N-α-chloroacetyl-N-(1,3-dioxolan-2-ylmethyl)-2-ethylaniline.

EXAMPLE 19

The dimethyl acetal of 3-chloropropionaldehyde + ethandiol-1,2 + 2,6-diethylaniline + chloroacetyl chloride = N-α-chloroacetyl-N-(1,3-dioxolan-2-ylethyl)-2,6-diethylaniline.

EXAMPLE 20

The dimethyl acetal of 2-chloroacetaldehyde + propandiol-1,2 + 2,4-dimethylaniline + bromoacetyl chloride = N-α-bromoacetyl-N-(4-methyl-1,3-dioxolan-2-ylmethyl)-2,4-dimethylaniline.

EXAMPLE 21

The dimethyl acetal of 2-chloroacetaldehyde + butandiol-1,2 + 2-propyl-4-bromoaniline + α-chloropropanoyl chloride = N-α-chloropropionyl-N-(4-ethyl-1,3-dioxolan-2-ylmethyl)-2-propyl-4-bromoaniline.

EXAMPLE 22

The dimethyl acetal of 2-chloroacetaldehyde + pentandiol-1,2 + 2,4,6-tributylaniline + chloroacetyl chloride = N-α-chloroacetyl-N-(4-propyl-1,3-dioxolan-2-ylmethyl)-2,4,6-tributylaniline.

EXAMPLE 23

The dimethyl acetal of 2-chloroacetaldehyde + hexandiol-1,2 + 2-methyl-6-methoxyaniline + α-chloroacetyl chloride = N-α-chloroacetyl-N-(4-butyl-1,3-dioxolan-2-ylmethyl)-2-methyl-6-methoxyaniline.

EXAMPLE 24

The dimethyl acetal of 2-chloroacetaldehyde + hexandiol-3,4 + 2,3-diethyl-6-ethoxyaniline + α-chlorobutanoyl chloride = N-α-chlorobutanoyl-N-(4,5-diethyl-1,3-dioxolan-2-ylmethyl)-2,3-diethyl-6-ethoxyaniline.

EXAMPLE 25

The dimethyl acetal of 2-chloroacetaldehyde + propandiol-1,3 + 2-methyl-4-iodoaniline + iodoacetyl chloride = N-α-iodoacetyl-N-(1,3-dioxan-2-ylmethyl)-2-methyl-4-iodoaniline.

EXAMPLE 26

The dimethyl acetal of 2-chloroacetaldehyde + butandiol-1,3 + 2-methyl-6-butoxyaniline + chloroacetyl chloride = N-α-chloroacetyl-N-(4-methyl-1,3-dioxan-2-ylmethyl)-2-methyl-6-butoxyaniline.

EXAMPLE 27

The dimethyl acetal of 2-chloroacetaldehyde + butandiol-1,4 + 2-propyl-4-ethylaniline + α-chlorohexanoyl chloride = N-α-chlorohexanoyl-N-(1,3-dioxepan-2-ylmethyl)2-propyl-4-ethylaniline.

EXAMPLE 28

The dimethyl acetal of 2-chloroacetaldehyde + ethandithiol-1,2 + 2,6-dimethylaniline + chloroacetyl chloride = N-α-chloroacetyl-N-(1,3-dithiolan-2-ylmethyl)2,6-dimethylaniline.

EXAMPLE 29

The dimethyl acetal of 2-chloroacetaldehyde + propandithiol-1,3 + 2,6-diethylaniline + chloroacetyl chloride = N-α-chloroacetyl-N-(1,3-dithian-2-ylmethyl)-2,6-diethylaniline.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 30

Preparation of a Dust

Product of Example 3     10
Powdered Talc            90

The above ingredients are mixed in a mechanical grinder-blender and are ground until a homogeneous, freeflowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5 to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atazine, trietazine, simetone, prometone, propazine, ametryne and the like; chloroacetamide herbicides such as alpha-chloro-N, N-dimethylacetamide, CDEA, CDAA, alpha-chloro-N-isopropylacetamide, 2-chloro-N-isopropylacetanilide, 4-(chloroacetyl)morpholine, 1-(chloroacetyl)piperidine, and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose-grass, chickweed, wild oats, velvetleaf, purslane, barnyard grass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morning glory, bedstraw, ducksalad and naiad; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and wintercress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about 1 or 2 ounces of active compound per acre may be sufficient for good control of a light infestation of weeds growing under adverse conditions, the application of 10 pounds or more of an active compound per acre may be required for good control of a dense infestation of hardy perennial weeds growing under favorable conditions.

The herbicidal activity of the compounds of this invention was demonstrated by experiments carried out for the pre-emergence control of a variety of weeds. In these experiments small plastic greenhouse pots filled with dry soil were seeded with the weed seeds. Twenty-four hours or less after seeding the pots were sprayed with water until the soil was wet and the test compounds formulated as aqueous emulsions of acetone solutions containing emulsifiers were sprayed at the indicated concentrations on the surface of the soil.

After spraying, the soil containers were placed in the greenhouse and provided with supplementary heat as required and daily or more frequent watering. The plants were maintained under these conditions for a period of from 25 to 35 days, at which time the condition of the plants and the degree of injury to the plants was rated on a scale of from 0 to 10, as follows: 0 = no injury, 1,2 = slight injury, 3,4 = moderate injury, 5,6 = moderately severe injury, 7,8,9 = severe injury and 10 = death. The effectiveness of these compounds is demonstrated by the following data:

TABLE I

| Test Compound | Concentration of Test Compound in lbs./acre | Yellow Nutsedge | Johnson Grass | Pigweed | Yellow Foxtail | Barnyard-grass | Crabgrass |
|---|---|---|---|---|---|---|---|
| Product of Example 3 | 10 | 10 | 9 | 10 | 10 | 10 | 10 |
|  | 4 | 10 | 9 | 10 | 9 | 10 | 10 |
|  | 2 | 10 | 10 | 10 | 9 | 9 | 10 |
|  | 1 | 10 | 8 | 10 | 8 | 9 | 9 |
| Product of Example 5 | 10 | 10 | 9 | 10 | 10 | 10 | 10 |
|  | 4 | 10 | 9 | 9 | 9 | 10 | 9 |
|  | 2 | 10 | 8 | 9 | 9 | 9 | 9 |
|  | 1 | 10 | 8 | 3 | 9 | 8 | 9 |
| Product of Example 18 | 10 | 9 | 2 | 10 | 10 | 10 | 5 |
|  | 4 | 10 | 1 | 10 | 9 | 9 | 7 |
|  | 2 | 10 | 0 | 9 | 9 | 8 | 5 |
|  | 1 | 10 | 0 | 3 | 8 | 4 | 4 |

We claim:

1. A herbicidal composition comprising an inert carrier and, as the essential active ingredient, in a quantity toxic to weeds, a compound of the formula

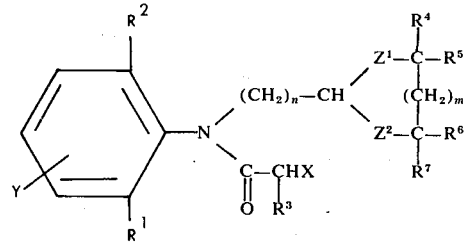

wherein Y is selected from the group consisting of hydrogen, lower alkyl and halogen; $R^1$ is selected from the group consisting of hydrogen, lower alkyl and lower alkoxy; $R^2$ is lower alkyl; $R^3$, $R^4$, $R^5$, $R^6$ and $R^7$ are independently selected from the group consisting of hydrogen and lower alkyl; X is halogen; m is the integer 1; $Z^1$ and $Z^2$ are oxygen; and n is an integer from 1 to 2.

2. The composition of claim 1 wherein the compound is N-α-chloroacetyl-N-(1,3-dioxan-2-ylmethyl)-2,6-dimethylaniline.

3. The composition of claim 1 wherein the compound is N-α-chloroacetyl-N-(1,3-dioxan-2-ylmethyl)-2,6-diethylaniline.

4. The composition of claim 1 wherein the compound is N-α-chloroacetyl-N-(4-methyl-1,3-dioxan-2-ylmethyl)-2-methyl-6-butoxyaniline.

5. A method of controlling weeds which comprises contacting said weeds with an effective amount of a herbicidal composition of claim 1.

6. A method of controlling weeds which comprises contacting said weeds with an effective amount of a herbicidal composition of claim 2.

7. A method of controlling weeds which comprises contacting said weeds with an effective amount of a herbicidal composition of claim 3.

8. A method of controlling weeds which comprises contacting said weeds with an effective amount of a herbicidal composition of claim 4.

* * * * *